(12) United States Patent
Kutty

(10) Patent No.: US 11,129,503 B2
(45) Date of Patent: Sep. 28, 2021

(54) ABRASIVE HYGIENE APPARATUS AND METHOD OF USE

(71) Applicant: Mymoona Kutty, Bourbonnais, IL (US)

(72) Inventor: Mymoona Kutty, Bourbonnais, IL (US)

(\*) Notice: Subject to any disclaimer, the term of this patent is extended or adjusted under 35 U.S.C. 154(b) by 396 days.

(21) Appl. No.: 16/297,370

(22) Filed: Mar. 8, 2019

(65) Prior Publication Data

US 2019/0274488 A1 Sep. 12, 2019

Related U.S. Application Data

(60) Provisional application No. 62/641,019, filed on Mar. 9, 2018.

(51) Int. Cl.
*A47K 7/02* (2006.01)
*A47K 3/00* (2006.01)
*A61B 17/54* (2006.01)
*A61H 35/00* (2006.01)

(52) U.S. Cl.
CPC .............. *A47K 7/026* (2013.01); *A47K 3/001* (2013.01); *A47K 3/002* (2013.01); *A61B 17/54* (2013.01); *A61H 35/006* (2013.01)

(58) Field of Classification Search
CPC ........ A47K 7/026; A47K 3/001; A47K 3/002; A61B 17/54; A61H 35/006
USPC ............................................................. 4/559
See application file for complete search history.

(56) References Cited

U.S. PATENT DOCUMENTS

| 1,747,269 | A | * | 2/1930 | Uhl | B43L 23/006 |
| | | | | | 451/491 |
| 2,680,334 | A | * | 6/1954 | Howard | B24D 15/023 |
| | | | | | 451/517 |
| 3,914,838 | A | * | 10/1975 | Coon | B23D 71/04 |
| | | | | | 407/29.15 |
| 4,377,057 | A | * | 3/1983 | Pincha | B24D 15/023 |
| | | | | | 451/491 |
| 10,646,257 | B2 | * | 5/2020 | Comstock | A61B 17/54 |
| 2015/0335356 | A1 | * | 11/2015 | Brooks | A61B 17/54 |
| | | | | | 606/131 |

\* cited by examiner

*Primary Examiner* — Tuan N Nguyen
(74) *Attorney, Agent, or Firm* — Singleton Law Firm, P.C.

(57) ABSTRACT

An abrasive non-pliable hygiene apparatus for smoothing a foot and method of use. The apparatus includes an abrasion sheet, frame, and engagement sheet. The abrasion sheet is composed of a non-pliable, corrosion-resistant material with a roughened top surface designed to increase abrasion efficiency between the sheet and an epidermal surface of a foot. The abrasion sheet also has bracketing members designed to engage the frame. The frame has ridge structures designed to retain the abrasion sheet and allow for user grip. Attached to the bottom of the frame, the engagement sheet facilitates friction, retaining the placement of the apparatus during use. The frame and abrasion sheet may be one structure, having at least one additional channel disposed along a side, allowing other abrasion sheets to be attached thereto.

14 Claims, 4 Drawing Sheets

ABRASIVE HYGIENE APPARATUS AND METHOD OF USE

CROSS-REFERENCE TO RELATED APPLICATIONS

This invention claims priority from the previously filed provisional application, U.S. Pat No. 62/641,019, filed Mar. 9, 2018; the contents of which are herein incorporated by reference.

BACKGROUND OF THE INVENTION

Podiatric scraping and smoothing devices have been utilized in the field of personal hygiene for many decades. Such devices comprise a rough surface with an accompanying handle and are rubbed or scraped across the bottom of the foot, in most circumstances the heel, to remove callouses, remove debris build-up, prevent dry or cracked skin formation, and promote skin exfoliation. The handheld nature of such devices presents a propensity to expose a user to precarious positions during the intended use. Many elderly users may even find use of such devices inconvenient or impossible and not worth the risk of accidental bodily harm. As such, floor-bound scrapers and smoothers comprising pliable yet abrasive surfaces were developed to allow a user to operate a scraper or smoother while in the sitting position. Such pliable abrasive surfaces are formed from various materials known to those of ordinary skill in the art, such as rubber, pumice stone, plastic molding, gravel, rock, or sand.

U.S. Pat. No. 6,530,096 to Mayhew et al. discloses an apparatus constructed of a lower surface that is releasably engaged with a floor and an upper portion with a selectively applicable upper surface for removing dead skin of a foot of a user. Mayhew's apparatus discloses a pliable mat where an abrasive portion is blended with the mat as an inherent feature; mounted to the mat by an adhesive; or secured to a lip of the mat.

Floor-bound abrasive hygiene apparatuses known in the art have not been readily manufactured to include non-pliable materials, such as metals or metal alloys. Non-pliable materials have a potential to increase abrasion efficiency between the abrasive surface and a user's foot. Additionally, various non-pliable materials do not experience deterioration rates as high as the pliable materials known in the art. This diminished deterioration potentially lowers or eliminates the replacement rate for such abrasive surfaces.

The apparatus of Mayhew et al. further discloses one or more conventional suction cups mounted on a lower surface of the apparatus, adapted for releasable connection with a floor of a bath or shower. The suction cups additionally comprise a tab for assisting in disengaging the suction cups with the floor. Mayhew further discloses utilization of a magnetic base adhered to a tile floor and then removably adhered to the apparatus.

Many floor-bound abrasive hygiene apparatuses known in the art also comprise a system of suction cups disposed on the underside of the apparatus designed to secure the apparatus to a floor. In many cases, the use of suction cups may result in varying degrees of reliability in anchoring an apparatus to a surface. Some suction cups allow for such a wide range of movement that the apparatus may be constructively and easily unattached from the surface. Such characteristics also tend to be more commonplace with suction cups after prolonged periods of use or age, warranting replacement. Other suction cups secure to a surface so rigidly as to render any positional adjustment of the apparatus considerably difficult if not impossible without extensive damage to the surface. Further, many devices known in the art use suction cups, adhesives, or frictional fitting in attaching individual components of an apparatus to one another. In addition to the above issues related to suction cups, adhesives disallow any adjustment or replacement of components and mere frictional fitting between surfaces could fail in the presence of elevated moisture levels such as in a bathroom, the main location of use known to the art.

Use of an engagement surface disposed upon an underside of an abrasive hygiene apparatus would present advantages in adjustably securing the apparatus both between and during uses. Adjustably securing the apparatus allows better and more sturdy operation by a user, in both a standing and sitting position. Additionally, alternative engagement structures between the components of an apparatus and a surface would support the overall efficacy of both function and stability, as well as prolonging the functional life of the apparatus itself.

SUMMARY OF THE INVENTION

The present invention relates to an abrasive non-pliable hygiene apparatus and method of use. The apparatus has an abrasion sheet made of a non-pliable material with a roughened top surface designed to increase abrasion efficiency between the sheet and an epidermal surface of a foot. The abrasion sheet further comprises bracket members projecting from opposing edges of a bottom surface of the abrasion sheet first downward and then inward towards a central planar axis of the sheet, forming an attachment channel with the abrasion sheet.

The bracket members and attachment channels function to removably couple a frame made of durable material designed to absorb and withstand considerable impact, such as a downward and lateral force of a foot. A plurality of grooves is further disposed upon a top surface, configured to allow decoupling of the abrasion sheet. The frame further comprises at least one ridge structure to retain the abrasion sheet to the frame and provide a gripping surface for a user. The ridge structures are configured such that, when the abrasion sheet is attached to the frame, they are adjacent to the bracket members but opposite one another.

Removably coupled to a bottom surface of the frame, the apparatus also includes an engagement sheet made of durable frictionally-enhanced material designed to facilitate grip between the frame and another surface.

DETAILED DESCRIPTION OF THE INVENTION

The foregoing features and advantages of the present invention are apparent from the subsequent detailed description of representative embodiments, read in conjunction with the attached drawings. The detailed description and drawings are illustrative of the invention rather than limiting, with the scope of the invention being defined by the appended claims and equivalents thereof.

The present invention relates to an improved podiatric hygiene apparatus with an abrasion sheet made of a non-pliable material and configured to improve abrasion efficiency between the sheet and a user's foot.

Figure 1:
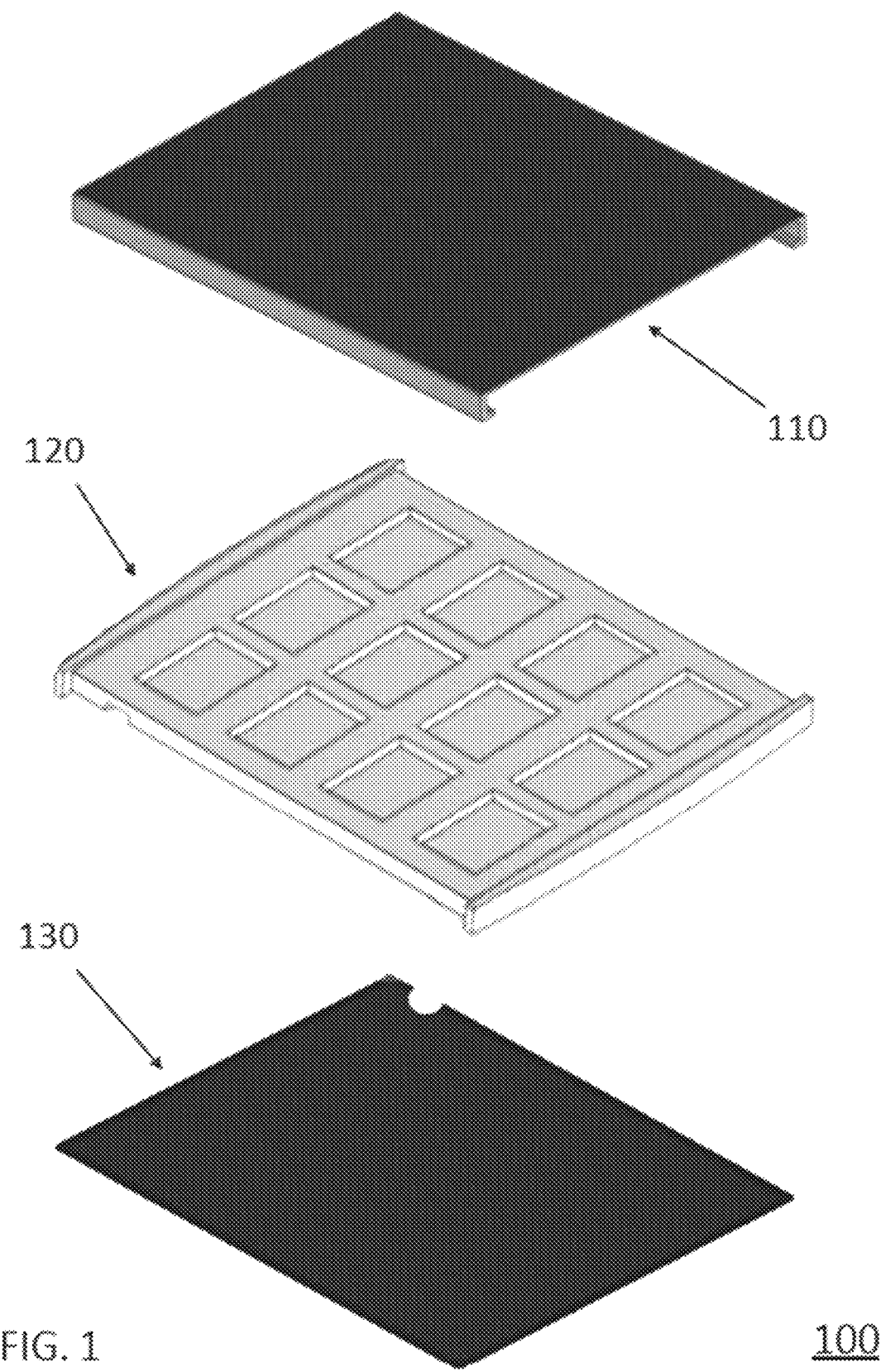
FIG. 1 illustrates an exploded view of the abrasive hygiene apparatus.
Figure 2:
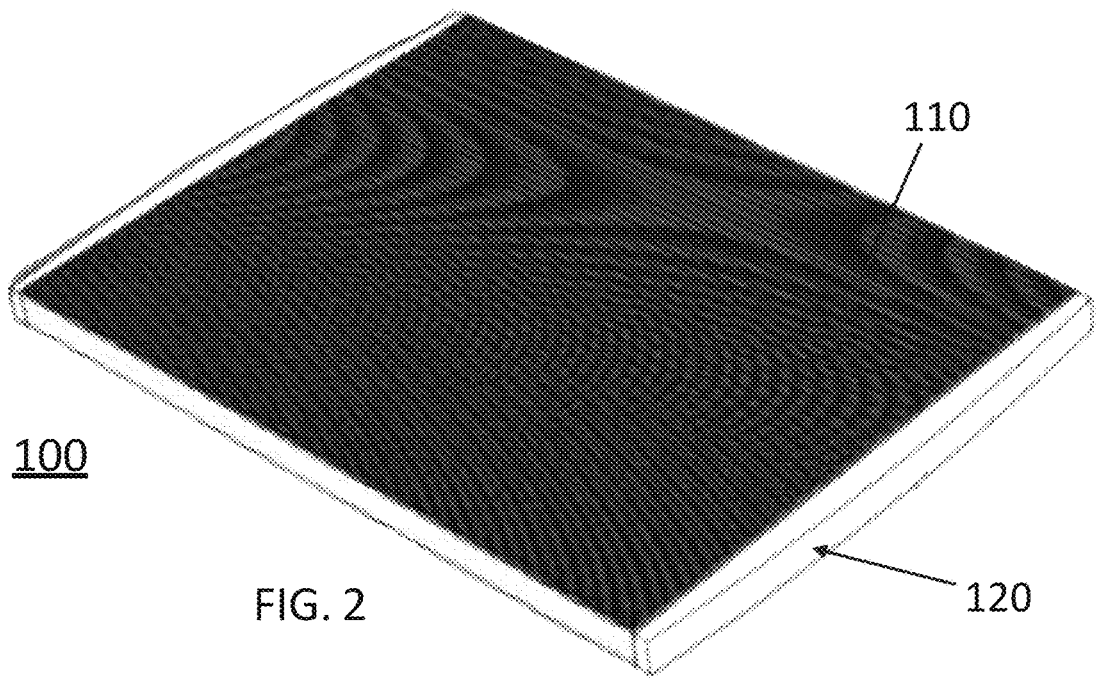
FIG. 2 illustrates a perspective view of the abrasive hygiene apparatus.

FIG. 1 presents an exploded view of the abrasive hygiene apparatus 100, comprising an abrasion sheet 110; a frame 120; and an engagement sheet 130. When fully assembled, as shown in FIG. 2, the abrasion sheet 110 of the apparatus 100 is removably coupled to a top surface of the frame 120, and the engagement sheet (not shown) is removably coupled to a bottom surface of the frame 120.

Figure 3:
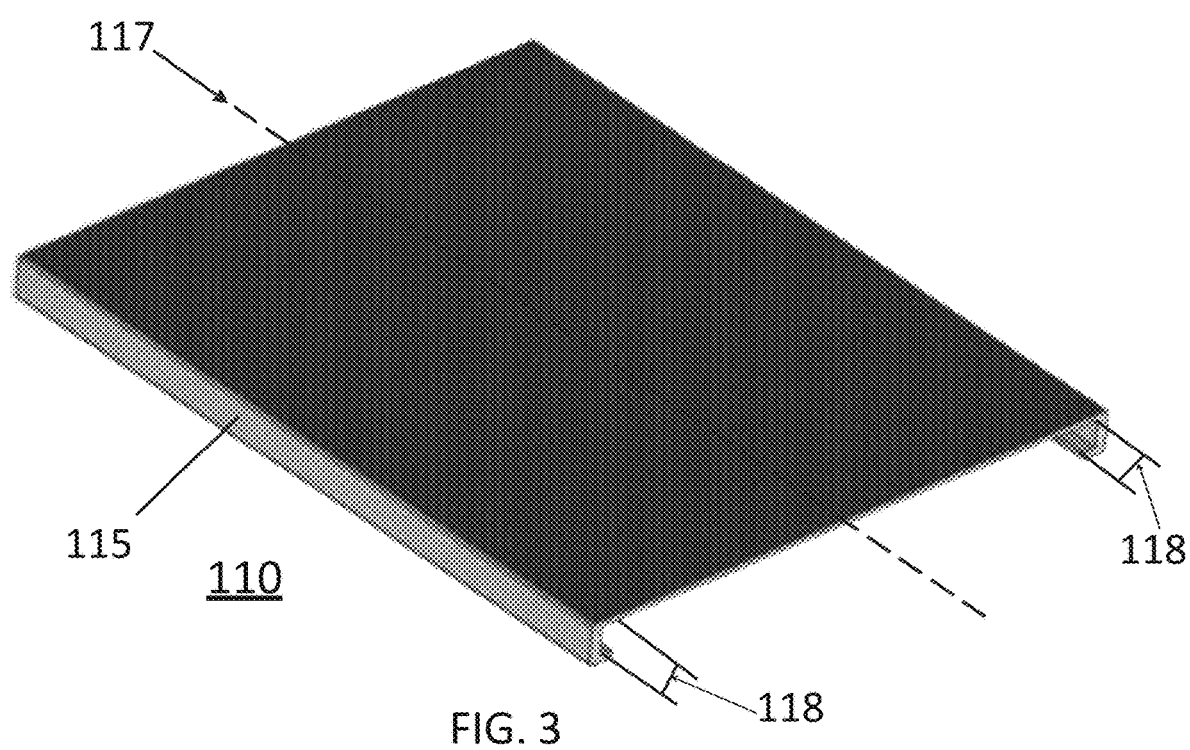
FIG. 3 illustrates a perspective view of the abrasion sheet of the abrasive hygiene apparatus.

The abrasion sheet 110 of the abrasive hygiene apparatus, shown in FIG. 3, comprises a top surface 111 and a bottom surface (not shown). The top surface 111 further comprises a roughened texture pattern composed of raised geometric structures including, but not limited to, pyramidal, hemispheric, trapezoidal, or irregular polygonal structures. A person of ordinary skill in the art would understand that the texture pattern may comprise a randomized mixture, gradient, hierarchal, homogenous, or uniformly continuous configuration of geometric structures. A person skilled in the art would also appreciate that the various pattern configurations may be disposed upon multiple abrasion sheets, based on a desired result by a user or manufacturer.

The abrasion sheet 110 is composed of a durable corrosion-resistant material, including but not limited to metal or metal alloy. The abrasion sheet is further configured to be non-pliable, promoting structural stability of the apparatus. A bottom surface (not shown) of the abrasion sheet 110 comprises at least one bracket member 115 extended from at least one edge of the abrasion sheet 110. At least one bracket member 115 projects first downward from the abrasion sheet 110 and then laterally towards a central planar axis of the abrasion sheet 117. The at least one bracket member 115 thus forms an attachment channel 118 with the abrasion sheet 110. The attachment channel 118 is configured to facilitate removable coupling of the abrasion sheet 110 to the frame 120.

Figure 4:
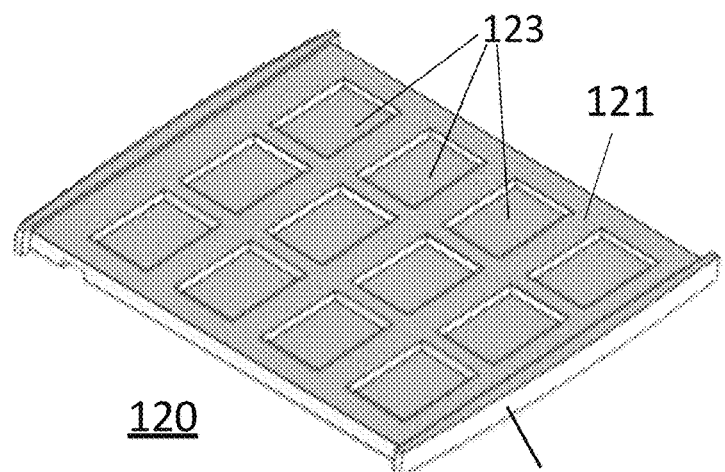
FIG. 4 illustrates a perspective view of the frame of the abrasive hygiene apparatus.
Figure 5:
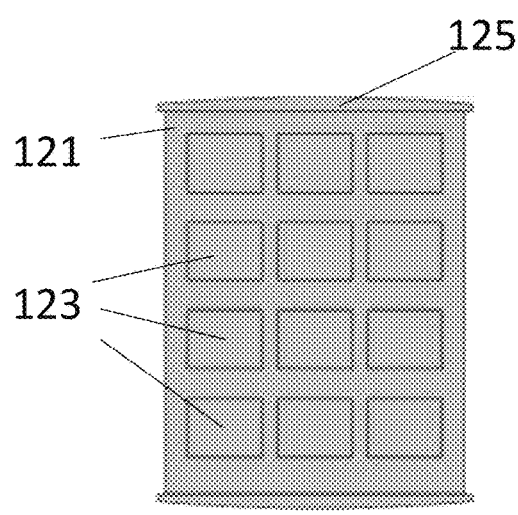
FIG. 5 illustrates a profile view of the frame of the abrasive hygiene apparatus.

The frame 120 of the abrasive hygiene apparatus 100, shown in FIGS. 4-5, comprises a top and bottom surface similarly dimensioned to that of the abrasion sheet 110, but may be marginally larger or smaller in some dimensions to facilitate coupling capabilities. The frame 120 further comprises a plurality of grooves 123 disposed upon the top surface 121 and configured to facilitate decoupling of the abrasion sheet 110 from the frame 120. The frame further comprises at least one ridge structure 125 coupled to at least one edge of the frame. At least one ridge structure 125 projects perpendicularly from a surface of the frame 120, configured to retain the abrasion sheet 110 to the frame 120. At least one ridge structure 125 is further configured to form a gripping surface for a user during adjustment and use of the apparatus 100.

The frame 120 is composed of an impact-resistant material, configured to absorb and withstand considerable amounts of impact forces and promote structural stability of the apparatus 100. Such substantial impact forces may include a downward or lateral force transferred by a foot of a user during use of the apparatus 100. A person skilled in the art would appreciate that suitable frame materials may include but are not limited to; polycarbonate (PC), polyphenylsulfone (PPSU), acrylonitrile butadiene styrene (ABS), or other durable thermoplastics.

Figure 6:
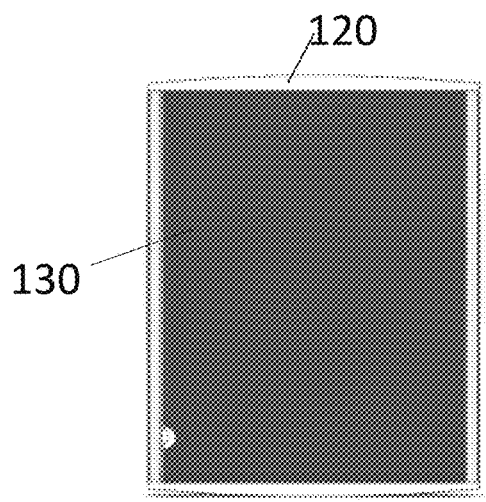
FIG. 6 illustrates a profile view of the engagement sheet coupled to the bottom surface of the abrasive hygiene apparatus.

The abrasive hygiene apparatus 100 further comprises an engagement sheet 130, shown in FIG. 6, removably coupled to the bottom surface (not shown) of the frame 120. The engagement sheet 130 comprises a top and bottom surface of similar dimensions to the abrasion sheet 110 and is configured to facilitate grip between the abrasive hygiene apparatus 100 and another surface. The engagement sheet 130 may be composed of any durable material with enhanced frictional characteristics, including by not limited to, polyvinyl chloride, polybutadiene, or styrene-butadiene. In some embodiments of the invention, the engagement sheet 130 may include an anti-slip coating such as a polyurea, a polyaspartic, or a polymeric aggregate coating.

In some embodiments of the invention, the abrasive hygiene apparatus 100 comprises a semi-circular slit disposed through both the engagement sheet 130 and the frame 120, configured to allow decoupling of an individual component from the rest of the assembled apparatus 100.

In some embodiments of the invention, the abrasion sheet 110 may be removed from the apparatus 100 and replaced with an abrasion sheet comprising a different surface texture pattern configuration, depending on current needs of the user.

Figure 7:
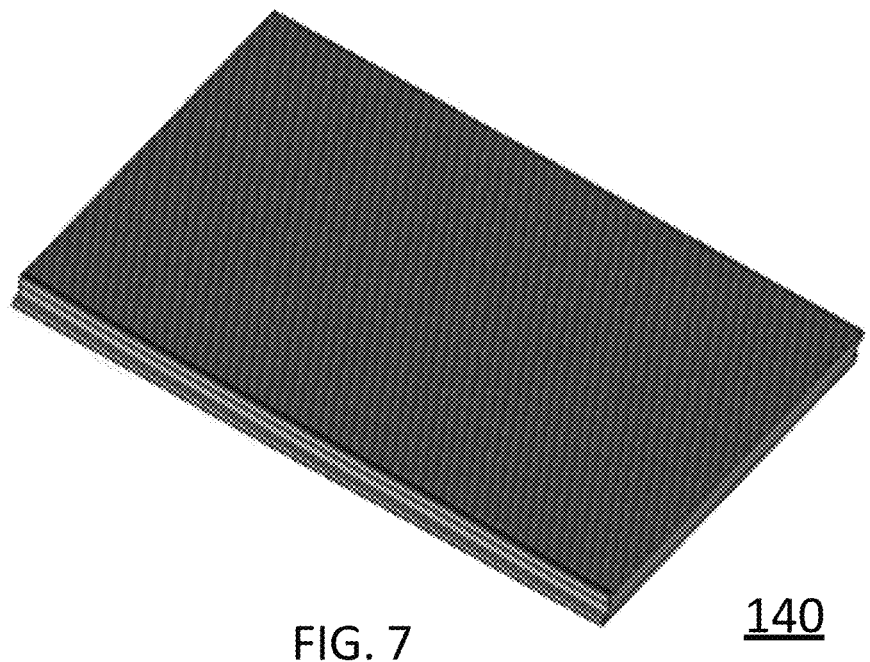
FIG. 7 illustrates a perspective view of an embodiment of the abrasive hygiene apparatus wherein the abrasive sheet and frame comprise a single structure.

In another embodiment of the invention, as shown in FIG. 7, the abrasion sheet 110 and the frame 120 may comprise a single structure 140, the top surface 121 of the frame 120 having a roughened texture pattern composed of raised geometric structures including, but not limited to, pyramidal, hemispheric, trapezoidal, or irregular polygonal structures. A person of ordinary skill in the art would understand that the texture pattern may comprise a randomized mixture, gradient, hierarchal, homogenous, or uniformly continuous configuration of geometric structures. The single structure 140 may be composed of a durable corrosion-resistant material, including but not limited to metal or metal alloy, and configured to be non-pliable, promoting structural stability of the apparatus.

Figure 8:
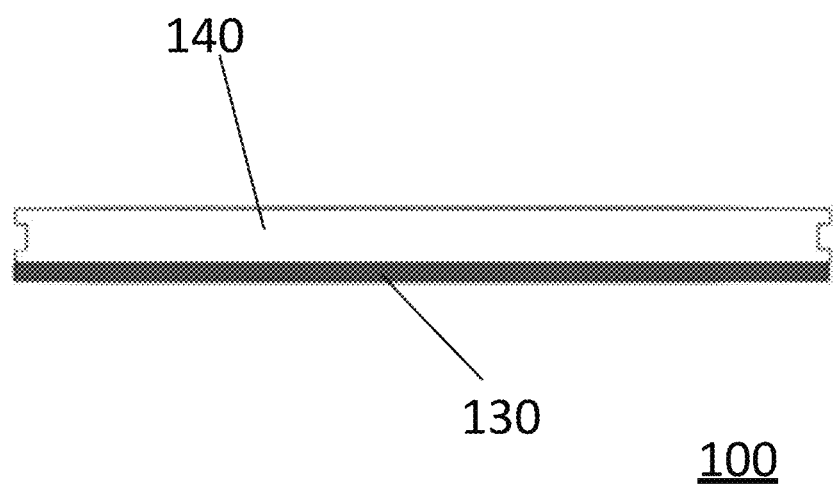
FIG. 8 illustrates a profile view of an embodiment of the abrasive hygiene apparatus wherein the abrasive sheet and frame comprise a single structure.

The single structure 140, as shown in FIG. 8, may further comprise at least one channel 145 disposed along at least one lateral surface. The at least one channel 145 is configured to facilitate user grip and allow a different abrasion sheet to be coupled thereto by engaging a bracket member 115 of the abrasion sheet 110 with the at least one channel 145 of the single structure 140. This configuration allows one abrasion sheet having a particular surface texture pattern to be used and stored atop a single structure having a different surface texture pattern to further allow user choice and interchangeability of multiple abrasion sheets with differing surface texture patterns.

The method of using the abrasive hygiene apparatus 100 comprises a user first placing the fully assembled apparatus upon a desired operating surface, such as a floor, engaging the engagement sheet 130 with the surface. The user then places a bare foot on the top surface of the abrasion sheet 110 of the apparatus, engaging an epidermal surface of the foot with the roughened surface of the sheet 110. The user then moves the foot laterally in multiple directions, facilitating abrasive interaction between the foot and the abrasion sheet 110. This action facilitates callous removal, debris build-up removal, dry or cracked skin prevention, and skin exfoliation promotion.

When finished, the user may disengage the foot from the apparatus. Next the user may then grip the ridge structures 125 of the frame 120 and remove the apparatus from the operating surface in preparation for cleaning or storage of the apparatus.

To perform cleaning, maintenance, or component replacement of the apparatus, the user may first disengage the engagement mat 130 from the frame 120. The user then disengages the abrasion sheet 110 from the frame 120. Once each component of the apparatus is disengaged from one another, and the apparatus disassembled, the user may then perform the desired cleaning, maintenance, or replacement. To reassemble the apparatus, the user may perform the aforementioned steps in reverse order until the apparatus is complete again. The above described steps for cleaning, maintenance, or replacement may be performed by a user in any desired order such that the result is a fully assembled or fully disassembled apparatus.

While the invention has been described with respect to various embodiments, it will be understood that the invention is capable of further modifications. This application is intended to cover any variations, uses, or adaptations of the invention generally following the principles of the invention, and includes such departures from the present disclosure within the known and customary practice in the art to which the invention pertains.

What is claimed is:

1. An abrasive hygiene apparatus, comprising:
   a. an abrasion sheet having a top surface and a bottom surface;
   b. a frame having a top surface, a bottom surface, and at least one ridge structure removably coupled to an edge;
   c. an engagement sheet having a top surface and a bottom surface;
   d. wherein the bottom surface of the abrasion sheet is removably coupled to the top surface of the frame;
   e. wherein the bottom surface of the frame is removably coupled to the top surface of the engagement sheet;
   f. wherein the engagement sheet further comprises a semi-circular slit disposed therethrough and along an edge of the engagement sheet, configured to allow decoupling of the engagement sheet from the frame; and
   g. wherein the frame further comprises a semi-circular slit disposed therethrough, configured to allow decoupling of the engagement sheet from the frame.

2. The abrasive hygiene apparatus of claim 1, wherein the abrasion sheet is composed of a corrosion-resistant material and is further configured to be non-pliable.

3. The abrasive hygiene apparatus of claim 1, wherein the frame is composed of an impact-resistant material, configured to promote structural stability of the apparatus.

4. The abrasion sheet of claim 1, wherein the top surface of the abrasion sheet further comprises a roughened texture pattern composed of raised geometric structures and configured to improve abrasion efficiency between the abrasion sheet and another surface.

5. The top surface of claim 4, wherein the roughened texture pattern further comprises a randomized mixture, gradient, hierarchal, homogenous, or uniformly continuous configuration of raised geometric structures.

6. The top surface of claim 4, wherein the raised geometric structures further comprise pyramidal, hemispheric, trapezoidal, or irregular polygonal structures.

7. The abrasion sheet of claim 1, wherein the bottom surface of the abrasion sheet further comprises at least one bracket member projecting downward from the abrasion sheet and inward towards a central planar axis of the abrasion sheet.

8. The abrasion sheet of claim 7, wherein the at least one bracket member forms an attachment channel with the bottom surface of the abrasion sheet, configured to couple and retain the frame to the abrasion sheet.

9. The frame of claim 1, wherein the top surface of the frame comprises a plurality of grooves periodically disposed thereupon and configured to facilitate decoupling of the abrasion sheet from the frame.

10. The frame of claim 1, wherein the at least one ridge structure projects perpendicularly from a surface of the frame, configured to retain the abrasion sheet to the frame.

11. The abrasive hygiene apparatus of claim 1, wherein the engagement sheet is composed of a material with enhanced frictional characteristics.

12. The abrasive hygiene apparatus of claim 1, wherein the engagement sheet further comprises an anti-slip coating.

13. The abrasive hygiene apparatus of claim 1, wherein the abrasion sheet and the frame comprise a single structure.

14. The abrasive hygiene apparatus of claim 13, wherein the single structure further comprises at least one channel disposed along at least one lateral surface, configured to couple a second abrasion sheet and facilitate user grip.

* * * * *